United States Patent
Fitzner et al.

(10) Patent No.: US 9,629,938 B2
(45) Date of Patent: Apr. 25, 2017

(54) EXHAUST GAS FILTER DEVICE

(71) Applicant: TZ Technisches Zentrum Entwicklungs- & Handelsgesellschaft mbH, Leipzig (DE)

(72) Inventors: Wigand Fitzner, Leipzig (DE); Klaus Döge, Dresden (DE)

(73) Assignee: TZ Technisches Zentrum Entwicklungs- und Handelsgesellschaft mbH, Leipzig (DE)

(*) Notice: Subject to any disclaimer, the term of this patent is extended or adjusted under 35 U.S.C. 154(b) by 179 days.

(21) Appl. No.: 14/417,177

(22) PCT Filed: Jul. 26, 2013

(86) PCT No.: PCT/DE2013/100276
§ 371 (c)(1),
(2) Date: Jan. 26, 2015

(87) PCT Pub. No.: WO2014/015862
PCT Pub. Date: Jan. 30, 2014

(65) Prior Publication Data
US 2015/0165083 A1    Jun. 18, 2015

(30) Foreign Application Priority Data

Jul. 26, 2012 (DE) .................. 10 2012 106 799
Dec. 6, 2012 (DE) .................. 10 2012 111 862
Jul. 24, 2013 (DE) .................. 10 2013 107 907

(51) Int. Cl.
*A61L 9/16* (2006.01)
*C12M 1/00* (2006.01)
(Continued)

(52) U.S. Cl.
CPC ............ *A61L 9/16* (2013.01); *B01D 46/0002* (2013.01); *B01D 46/0036* (2013.01);
(Continued)

(58) Field of Classification Search
CPC ................ A61L 9/16; B01D 2253/102; B01D 2253/116; B01D 2257/90;
(Continued)

(56) References Cited

U.S. PATENT DOCUMENTS 4,969,936 A * 11/1990 Schweigert .......... B01D 46/125
    96/129
6,319,298 B1    11/2001 Ng-Gee-Quan
(Continued)

FOREIGN PATENT DOCUMENTS

DE    3634377 A1    4/1987
DE    4326553 A1    2/1995
(Continued)

*Primary Examiner* — Michael Hobbs
(74) *Attorney, Agent, or Firm* — Michael Soderman (57) ABSTRACT

The invention relates to an exhaust gas filter device for filtering contaminants out of exhaust gases, comprising: a filtering apparatus for filtering the exhaust gases, wherein the exhaust gases enter the filtering apparatus at a filter inlet surface, flow through the filtering apparatus and exit the filtering apparatus at a filter outlet surface; and a distribution channel for distributing the exhaust gases to be filtered along the filter inlet surface, and a collection channel for collecting the filtered exhaust gases exiting at the filter outlet surface; wherein the cross section of the collection channel increases in the direction of flow of the exhaust gases and/or the cross section of the distribution channel decreases in the direction of flow of the exhaust gases.

11 Claims, 6 Drawing Sheets

(51) Int. Cl.
  *B01D 46/00*   (2006.01)
  *B01D 46/42*   (2006.01)
  *B01D 53/04*   (2006.01)
  *B01D 53/26*   (2006.01)

(52) U.S. Cl.
  CPC ..... *B01D 46/0038* (2013.01); *B01D 46/0041* (2013.01); *B01D 46/0047* (2013.01); *B01D 46/4263* (2013.01); *B01D 53/04* (2013.01); *B01D 53/26* (2013.01); *B01D 2253/102* (2013.01); *B01D 2253/116* (2013.01); *B01D 2257/90* (2013.01); *B01D 2259/40001* (2013.01); *B01D 2259/45* (2013.01)

(58) Field of Classification Search
  CPC ...... B01D 2259/40001; B01D 2259/45; B01D 46/0002; B01D 46/0036; B01D 46/0038; B01D 46/0041; B01D 46/0047; B01D 46/4263; B01D 53/04; B01D 53/26
  USPC ...................................................... 435/283.1
  See application file for complete search history.

(56) References Cited

U.S. PATENT DOCUMENTS

| | | |
|---|---|---|
| 2003/0121240 A1 | 7/2003 | Hung |
| 2005/0011171 A1 | 1/2005 | Lee et al. |
| 2006/0201119 A1* | 9/2006 | Song .................. A61L 9/16 55/471 |
| 2008/0053047 A1* | 3/2008 | Studer ................ B01D 46/24 55/471 |
| 2009/0010801 A1* | 1/2009 | Murphy ............ B01D 46/0028 422/4 |
| 2009/0032459 A1* | 2/2009 | Tanabe ................ C02F 9/00 210/615 |
| 2009/0193773 A1 | 8/2009 | Sundvik et al. |

FOREIGN PATENT DOCUMENTS

| | | |
|---|---|---|
| DE | 19913181 A1 | 9/2000 |
| DE | 102004027354 A1 | 2/2006 |
| EP | 1426237 A1 | 6/2004 |
| WO | 2010092178 A1 | 8/2010 |

* cited by examiner

EXHAUST GAS FILTER DEVICE

CROSS-REFERENCE TO RELATED APPLICATIONS

This application is the U.S. national stage of International Application No. PCT/DE2013/100276 filed on Jul. 26, 2013, and claims the benefit thereof. The application claims the benefit under 35 USC 119 of German Application Nos. DE 102012106799.6 filed on Jul. 26, 2012; Oct. 1, 2009; DE 102012111862.0 filed on Dec. 6, 2012 and DE 102013107907.5 filed on Jul. 24, 2013; all applications are incorporated by reference herein in their entirety.

BACKGROUND

The invention relates to a gas filter device for filtering contaminants (e.g. odorous substances) out of gases, e.g. to be used to neutralize odors from gases arising in sewage treatment engineering or other processes.

Gas filter devices usually have a filter unit; gases to be filtered flow through the filter unit and are filtered in the process. A filter unit of this type can filter solids out of a gas flow, for instance via mechanical actions. Furthermore, a filter unit of that type can bind to a substantial amount of noxious gases via absorption or adsorption until its capacity is exhausted with regard to that and a break-out of noxious gases comes about. There can be provisions, for instance, for the components that are to be removed from the gas flow to be "washed" or "stripped" (with vapor instead of liquid) via a suitable liquid in the absorption phase. As a different example, the constituent parts of the components to be removed can be selectively bound—usually in piles of granulate (e.g. molecular sieves or activated charcoal) or via mats to which an adsorbent is applied. Physical and chemical binding forces are the decisive parameters in the process; the effectiveness of the bonds are dependent, for example, on the gas temperature, the gas moisture content and the pressure. Biological components (e.g. microorganisms) can be added or can form during absorption and also during adsorption. That can lead so far in the process that the biological components provide the decisive forces and dominate the physical or chemical processes. The filter unit can be designed in the form of a biological filter unit, for instance; microorganisms (e.g. fungi or bacteria) use materials that are to be filtered out and that are contained in the gas stream as a nutrient—i.e. they metabolize them—and break them down in the process. The filter unit has a limited filtering capacity. Since a replacement of the used filter unit by an unused filter unit is appropriate as soon as the used filter unit has lost its filtering effect in a position (even if a filtering effect still exists in other positions), an even contaminant load across the filter unit and even filtering activity or an even filtering rate across the filter unit with an even distribution of the contaminants in the gases that are to be filtered out is advantageous for utilization of this filtering capacity that is as complete as possible.

SUMMARY

The invention relates to a gas filter device for filtering contaminants out of gases, comprising: a filtering apparatus for filtering the gases, wherein the gases enter the filtering apparatus at a filter inlet surface, flow through the filtering apparatus and exit the filtering apparatus at a filter outlet surface; and a distribution channel for distributing the gases to be filtered along the filter inlet surface, and a collection channel for collecting the filtered gases exiting at the filter outlet surface; wherein the cross section of the collection channel increases in the direction of flow of the gases and/or the cross section of the distribution channel decreases in the direction of flow of the gases.

DETAILED DESCRIPTION

A gas filter device that can be used in diverse ways and that can have a compact design with an uncomplicated structure is created by the invention; effective use of the filtering capacity of a filtering apparatus of the gas filter device is made possible in that way.

A gas filter device for filtering out contaminants, e.g. odorous substances, from gases that has a filtering apparatus for filtering the gases is provided for this as per the invention. The gas can be waste air, for instance, that is loaded with contaminants in the form of noxious gases. The gas filter device is especially intended to be used outside. The gas filter device is designed in such a way that the gases to be filtered enter the filtering apparatus at a filter inlet surface of the filtering apparatus, they flow through the filtering apparatus at a flow velocity and are filtered or cleaned in the process, and the filtered gases exit the filter apparatus at a filter outlet surface of the filtering apparatus.

The gas filter device has a distribution channel for distributing the gases to be filtered along the filter inlet surface and a collection channel for collecting the filtered gases exiting at the filter outlet surface. The collection channel is designed with a cross section that increases in the direction of flow of the gases flowing through it (that is to say along the longitudinal direction of the collection channel); the collection channel can be designed, for instance, with a cross-sectional area that increases in a continuous fashion (e.g. evenly) over its entire length or in a step-by-step fashion. The collection channel is preferably designed with a cross section that evenly increases along its entire length in the direction of flow such that a (constant) opening angle between 2° and 10° is enclosed by the side walls of the collection channel along the direction of flow. Alternatively, or in addition, the distribution channel is designed with a cross section that decreases in the direction of flow of the gases flowing through it (that is to say along the longitudinal direction of the distribution channel); the distribution channel can be designed, for instance, with a cross-sectional area that decreases in a continuous fashion (e.g. evenly) over its entire length or in a step-by-step fashion. The distribution channel is preferably designed with a cross section that evenly decreases along its entire length in the direction of flow such that a (constant) opening angle between 2° and 10° is enclosed by the side walls of the distribution channel along the direction of flow. There can, however, also be provisions for the distribution channel—when the collection channel is designed with a cross section that increases in the direction of flow of the gases—to be designed with a cross section that is constant or increasing in the direction of flow of the gases flowing through it.

An equalization of the flow velocities (i.e. the flow velocity at which the gases flow through the filtering apparatus) existing over the filter inlet surface is brought about (vis-a-vis a design of the collection channel and the distribution channel with a spatially constant cross section) by designing the collection channel and/or the distribution channel with the spatially varying cross sections described above; the flow characteristics of the gas filter device (resulting from the geometry of these channels) can be adjusted in such a way that the gases flow through the entire filtering apparatus or over the entire filter inlet surface at (essentially) the same flow velocity through the filtering apparatus. A corresponding equalization of the quantity of contaminants to be filtered out that arises per unit area of the filtering apparatus can be achieved because of that (with an even distribution of the contaminants in the gases to be filtered out), so effective utilization of the filtering capacity of the filtering apparatus is made possible.

Moreover, an effective use of space, filing out as much volume as possible in the gas filter device with filter elements and with a specified overall volume of the gas filter device, requires a design of the distribution channel and of the collection channel with a correspondingly small cross section; an uneven spatial velocity of the flow velocity over the filter inlet surface is brought about due to flow-related principles in the design of these channels with a spatially constant (small) cross section, wherein strongly differing flow velocities exist at different positions of the filtering apparatus or the filter inlet surface and different quantities of contaminants to be filtered out consequently also correspondingly arise. In contrast, an equalized flow velocity can also be realized when there is a design of these channels with a small cross-sectional area by designing the collection channel and/or the distribution channel with a varying cross section as described above, a compact (i.e. space-saving) and simultaneously effective gas filter device is made possible because of that.

The spatial equalization of the flow velocity is brought about, for instance, by having the volume of the collection channel also increase with an increasing volume of collected, filtered gases in the collection channel. The cross section of the collection channel and/or of the distribution channel can be varied via a molded part arranged in the flow path of the gases, for instance.

The distribution channel and the collection channel can be designed with a small cross section while maintaining a small spatial variation of the flow velocity via the design features that were described. In accordance with one design, the cross-sectional area (e.g. the mean value or the maximum value of the cross-sectional area) of the distribution channel and/or the cross-sectional area (e.g. the mean value or the maximum value of the cross-sectional area) of the collection channel is smaller than 5% of the filter inlet surface. In this design variant, the design of the collection channel and/or distribution channel with an opening angle of 3° has proven to be especially advantageous. The gas filter device can (via a corresponding design variant of the collection channel and/or the distribution channel) be designed in such a way, for instance, that the flow velocities at all of the positions of the filter inlet surface have a maximum deviation of 30%, 20% or even 10% of the (spatial, obtained by averaging across the filter inlet surface) mean value of this mean value.

The gas filter device can have a housing with an inlet opening for accommodating the gases to be filtered and an outlet opening for discharging the filtered gases; the gas filter device can, moreover, have an inflow channel running from the inlet opening to the filter inlet surface to feed the gases to be filtered into the filtering apparatus and an outflow channel running from the filter outlet surface to the outlet opening to discharge the filtered gases from the filtering apparatus. In accordance with the terminology used here, the distribution channel is the section of the inflow channel along which the gases to be filtered are distributed over the filter inlet surface and where they enter the filtering apparatus; the filter inlet surface in this section can define or form a (permeable) limitation surface of the inflow channel, for instance. The distribution channel can be a portion of the inflow channel or can be identical to the inflow channel. The collection channel is the section of the outflow channel along which the gases exiting the filter outlet surface are discharged from the filtering apparatus and collected; the filter outlet surface in this section can define or form a (permeable) limitation surface of the outflow channel. The collection channel can be a portion of the outflow channel or can be identical to the outflow channel.

The gas filter device can have an air conveyor (e.g. a fan or a blower) to convey the gases through the filtering apparatus. The air conveyor can be arranged at the inlet opening of the housing, for instance; it becomes possible to use the heat losses of the air conveyor to heat up the gases because of that.

In accordance with one embodiment, the filtering apparatus is equipped (e.g. filled) with microorganisms to break down or metabolize the contaminants. The filtering apparatus can have an activated-charcoal layer (e.g. in the form of an activated-charcoal mat), for instance, to absorb the contaminants to be filtered out; the activated-charcoal layer can be equipped or more precisely filled with the microorganisms. A storage and buffering effect can be achieved with the activated-charcoal layer because the contaminants to be filtered out are accumulated or stored in the activated charcoal and the activated-charcoal layer is regenerated via the microorganisms due to the fact that the stored contaminants are broken down by the microorganisms. The filtering apparatus can, however, also have other filter materials or filter mats (e.g. supplied with microorganisms), for instance to break down hydrogen sulfide. The respective filter mats can also be arranged in multiple layers. With the appropriate process management, the components can also simultaneously be separated from the gas flow in complex absorptive, adsorptive and biological ways.

In accordance with a further embodiment, the gas filter device also has a heating device to heat the gases to be filtered. Because the gases are heated by the heating device, the relative moisture content of the gases can be reduced without condensation before they enter the filtering apparatus; precipitation of water or moisture in the filtering apparatus, for instance, can be effectively suppressed because of that. Moreover, because of the reduction of the relative moisture content, the moisture existing in the area of the microorganisms or microbes can be regulated when the filtering apparatus is designed in the form of a biological filtering apparatus with microorganisms. The heating device can be designed, for instance, in such a way that the gases to be filtered are heated up by it to a specified temperature within the metabolizing temperature range of the microorganisms, for instance, before they enter the filtering apparatus (i.e. within the temperature range in which the microorganisms are capable of metabolizing the contaminants). Alternatively, or in addition, the heating device can be designed in such a way that the gases to be filtered are heated by it such that the resulting (relative) moisture content of the gases is within the metabolizing moisture range of the microorganisms (i.e. within the moisture range in which the microorganisms are capable of metabolizing the contaminants). The gas filter device can, in particular, be designed without a cooling device—e.g. provided to condense and precipitate liquid—for cooling the gases; an energy-intensive reheating of the gases before entering the filtering apparatus, as an example, can be avoided because of that.

Since the gas volume to be locally heated per unit of time by a portion of the heating device varies when there are flow velocities that differ on a local basis, different flow velocities lead to partial flows with different temperatures and consequently to corresponding spatial temperature differences that arise across the filtering apparatus. Because the flow velocity at which the gases flow through the filtering apparatus is equalized as described above, spatial temperature differences arising across the filtering apparatus that are brought about by flow velocities that differ on a local basis can therefore also be balanced out, at least in part, so essentially the same temperature exists at all of the positions of the filtering apparatus. Since the biological activity or feeding activity of the microorganisms varies with the temperature, a temperature that has been equalized across the filtering apparatus makes correspondingly equalized feeding activity or filtering activity of the microorganisms possible and consequently (with a uniform distribution of the microbes or microorganisms over the filtering apparatus) a correspondingly equalized filter rate; effective utilization of the filtering capacity of the filtering apparatus is given additional support because of that. Moreover, it can be ensured via the heating device that the microorganisms can always be kept within their metabolizing-temperature range regardless of environmental conditions or outside temperatures existing outside of the gas filter device; the gas filter device can be used in diverse ways independently of the external environmental conditions to a great extent because of that. The spatial equalization of the filtering activity (feeding activity of the microorganisms) can consequently also be supported in addition to the spatial equalization of the filter load (quantity of contaminants accumulating per section of the filtering apparatus) via the equalization of flow velocities described above.

The heating device can be an unregulated heating device, i.e. a heating device with heating power that cannot be varied (e.g. when the temperature of the gases to be filtered and/or the outside temperature at the place of use has a sufficiently low level of variation). The heating device can, however, also be an adjustable heating device; the heating power can be variably set (e.g. on the basis of the output value of a temperature sensor and/or moisture sensor positioned in the flow path of the gases to be filtered). The heating device can also be provided to directly heat the filtering apparatus (e.g. arranged in direct contact with same).

In accordance with one embodiment, the heating device is arranged in the flow path of the gases to be filtered, i.e. in front of the filtering apparatus with reference to the direction of flow. In accordance with this embodiment, merely the gases to be filtered have to be brought to the right temperature by the heating device (and, for instance, not the entire gas filter device). The heating device can, for instance, be arranged in the distribution channel and can, as an example, be in contact with the filtering apparatus (in that case, the filtering apparatus and consequently the microorganisms, for example, can be directly brought up to the right temperature by the heating device). Alternatively, or in addition, there can also be provisions for a heating element of the heating device to be arranged at the output of the air conveyor (or, as the case may be, at the input of the inflow channel). In particular, the heating device can be arranged and designed in such a way that a spatially uniform heat input per unit area is generated by it (i.e. the heating power does not vary locally) over a complete flow cross section of the gases— e.g. across a complete cross-sectional area of the inflow channel, especially the distribution channel.

In accordance with one embodiment, the heating device is an electrically operated heating device. There can be provisions, for instance, for the heating device to be designed in the form of a metallic heating network or in the form of a capillary-tube mat (wherein the capillary-tube mat can form a closed water circulation system, for instance, wherein the water of the water circulation system can be brought up to the right temperature via electrical means).

Furthermore, the gas filter device can have a heating element arranged in the flow path of the filtered gases, i.e. after the filtering apparatus with reference to the direction of flow (e.g. in the collection channel); this heating element can be designed in an analogous way to the heating device arranged in front of the filtering apparatus with reference to the direction of flow. The filtering apparatus and consequently the microorganisms as well if applicable can be additionally protected against external temperature influences via this heating element downstream to the filtering apparatus.

In accordance with one design, the gas filter device has at least one support mesh to hold the filtering apparatus; the filtering apparatus or at least a section of the filtering apparatus is fastened in a detachable way to the support mesh, forming a packet, and the packet that is formed in that way is arranged so as to be able to swivel around a horizontal axis. There can be provisions, as an example—especially when the filtering apparatus is designed with a polygonal horizontal cross section—for the filtering apparatus (or a section of the filtering apparatus, e.g. a filter mat), the heating device (or a heating element of the heating device) and a support mesh to be designed as one packet; this packet (after opening the housing of the gas filter device, if applicable) can be swiveled around an horizontal axis located at the lower end section of the packet. The filtering apparatus can be exchanged in an uncomplicated way because of that, for instance during maintenance work, by swiveling the packet from a vertical orientation to a horizontal orientation or folding it outwards and then replacing the filtering apparatus. There can be provisions, for example, for the horizontal axis to be connected on one side to the lower end section of the support mesh and on the other side to the housing of the gas filter device.

In accordance with one embodiment, the distribution channel is designed and arranged in such a way that the gases to be filtered will flow along the filter inlet surface in the distribution channel before they enter the filtering apparatus, i.e. the direction of flow of the gases to be filtered (essentially) runs in parallel with the filter inlet surface. As an example, the distribution channel can be arranged to have its longitudinal direction run along (or essentially in parallel with) the filter inlet surface. The collection channel can be designed and arranged in such a way that the filtered gases flow along the filter outlet surface in the collection channel after exiting the filtering apparatus, i.e. the direction of flow of the filtered gases is (essentially) in parallel with the filter outlet surface. The collection channel can, for example, be arranged for its longitudinal direction to run along (or essentially in parallel with) the filter outlet surface.

In accordance with these design forms, an effective use of space is made possible with a large filter area for a specified overall volume of the gas filter device. There can be provisions, for instance, for the filtering apparatus to be designed with a closed, run-around contour (e.g. in the form of a hollow cylinder), e.g. by rolling together an activated-charcoal met into a hollow cylinder; the interior space of the filtering apparatus acts as a distribution channel or a collection channel and is connected to the other respective channel outside of the filtering apparatus.

In accordance with one embodiment, the filtering apparatus, the distribution channel, the collection channel and the heating device are arranged in a housing; at least one part of the outer wall of the housing or the entire outer wall of the housing has thermal insulation. Because the gas filter device is thermally insulated vis-a-vis the outside, the gases can be brought up to the right temperature by the heating device (essentially) independently of the outside temperature, so the heating device can be designed in the form of an unregulated heating device, for instance. Moreover, the freezing of moisture condensing on the housing wall can be prevented via the thermal insulation. Furthermore, the thermal insulation supports the equalization of the temperature of the gases to be filtered by preventing the thermal coupling or, or more precisely, heat losses to the external environment.

The gas filter device can also be insulated against the influence of weather via flow-related shielding. The flow-related shielding can be realized, as an example, by arranging (e.g. at a specific height) and designing (e.g. with a specific cross-sectional area) the outlet opening through which the filtered gases escape from the gas filter device in such a way that the excess pressure of the filtered gases is higher at the outlet opening than the wind pressure at the height of the outlet opening, and the gases exiting the outlet opening will consequently form a flow-related shield of the gas filter device.

The housing can be closed at the top in such a way that penetration of rainwater is reliably prevented. Moreover, the housing can be designed in such a way that any condensation water that may accumulate on the outer surface or the outer wall of the housing can run off (and, for instance, can run downwards out of the housing through openings provided for that).

The gas filter device can be designed to be an independent, freestanding cell or filter cell. There can also be provisions, however, for the gas filter device to be integrated into a building; parts of the gas filter device are formed by the building or by components that are already on or in the building, and the gas filter device and the building are therefore integrally designed with one another, at least in part. Because the gas filter device is integrated into a building, using building components that already exist, the gas filter device can be realized and integrated into the building at low cost (in particular with lower costs than is the case with a design as an autonomous freestanding cell).

With building integration of that type, the same filtering apparatus (e.g. filtering apparatus/activated-charcoal mats supplied with microorganisms), support meshes and/or heating devices can be used as is the case with a freestanding cell; the filtering apparatus, the support mesh and a heating device can be connected to each other (in a detachable way), for instance, forming a filter packet or filter stack. These filter packets can be advantageously arranged in a building with a distribution channel and a collection channel.

There can be provisions, for instance, for the functions of the housing, the ventilation hood, the inlet opening, the outlet opening, the air conveyor (a natural draft, e.g. natural air flow based on the temperature or height differences, can also be used if necessary) and/or the thermal insulation layer of the gas filter device can be taken over in whole or in part by corresponding components of a building. Production halls, housing enclosures for facilities generating gas, animal stalls etc. can be buildings of this type. In part, these building already have fans, air-conditioning units, heat sources, adequate thermal insulation etc. that already fulfill the applicable regulations (e.g. TA-Lärm, the noise abatement code). The functions of the gas filter device that have not yet been fulfilled by the building have to be added in a suitable way.

There can be provisions, for instance, for the collection channel to be formed between a wall—e.g. a vertical wall (for instance an outer wall or partition wall) or a roof—of the building and the filter outlet surface and/or the distribution channel to be formed between a wall of the building and the filter inlet surface. As another example, there can be provisions for the distribution channel to be comprised of a (relatively large) room or a room of the building from which the gases or waste air to be filtered flows directly into the filtering apparatus (supplied with microorganisms, for instance).

BRIEF DESCRIPTION OF THE DRAWINGS

The invention will be illustrated below with the aid of examples with a reference to the figures that have been included, wherein the same or similar features are provided with the same reference numerals; the following are shown schematically here.

DETAILED DESCRIPTION OF THE PREFERRED EMBODIMENTS

Figure 1A:
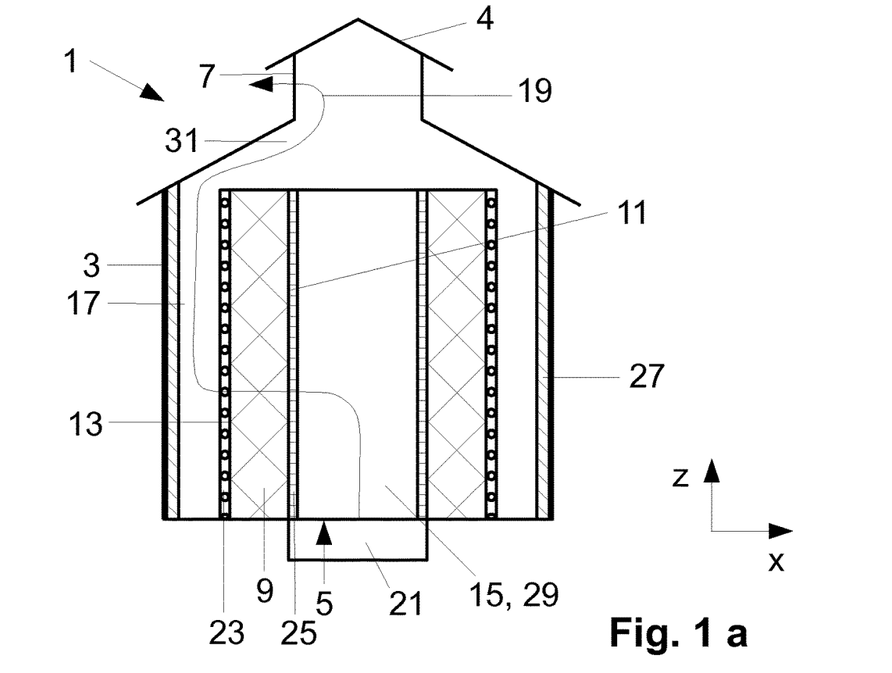
FIG. 1a shows a sectional view of a gas filter device with a distribution channel and a collection channel with a constant cross section.
Figure 1B:
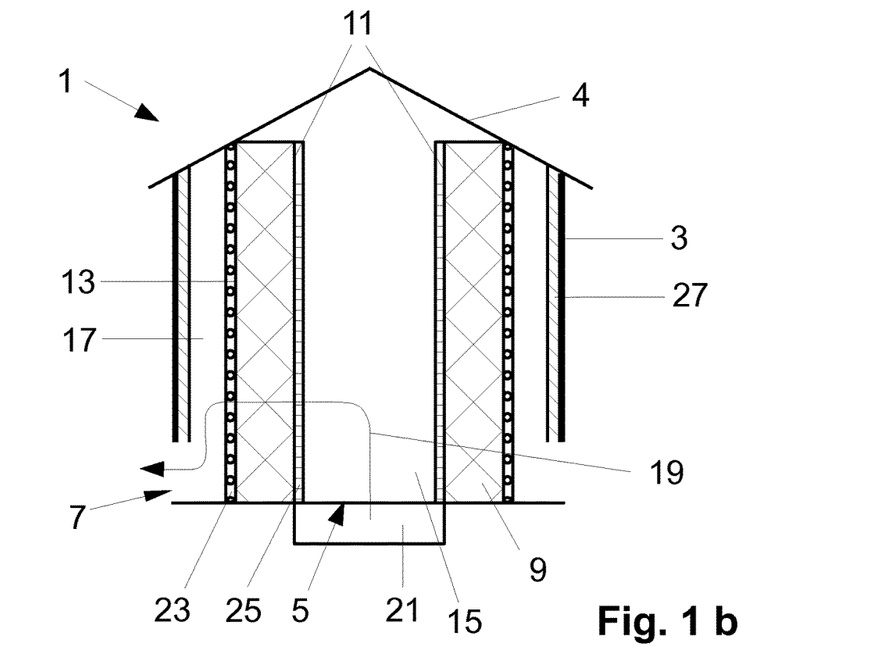
FIG. 1b shows a sectional view of another gas filter device with a distribution channel and a collection channel with a constant cross section.

FIGS. 1a and 1b illustrate for comparative purposes a gas filter device 1 with a distribution channel and a collection channel in each case; the distribution channel and the collection channel each have a constant cross section that remains the same in a spatial sense. FIGS. 2 to 8 each illustrate embodiments of a gas filter device 1 as per the invention; the distribution channel and/or the collection channel is designed with a spatially varying cross section. In accordance with FIGS. 1a to 4e, the gas filter device 1 has a housing 3 with an inlet opening 5 to take in the gases to be filtered and an outlet opening 7 to discharge filtered gases; the outlet opening 7 is provided with an outlet grid, as an example (e.g. for protection against the penetration of impurities). In accordance with FIGS. 1a to 4e, the gas filter device 1 is designed to be a rain-tight freestanding cell via a corresponding design of the housing 3 and is intended to be used outside; the housing has, as an example, a roof section or a ventilation hood 4 that is designed in such a way that penetration of rainwater is reliably prevented. The vertical direction or direction of a plumb line runs along the z direction of the xz coordinate system shown as an example in FIGS. 1a and 2. In accordance with FIGS. 5 to 8, the gas filter device 1 is integrated into a building 45 in each case.

The gas filter device 1 has a filtering apparatus 9 in each case for filtering contaminants in the form of odorous substances out of the gases; the gases to be cleaned enter the filtering apparatus 9 at a filter inlet surface 11 of the filtering apparatus 9, flow through the filtering apparatus 9 and exit the filtering apparatus 9 at a filter outlet surface 13. The filtering apparatus 9 is comprised of one or more activated-charcoal mats 9 that are filled with microorganisms to break down the contaminants.

The gas filter device 1 has a distribution channel 15 for distributing the gases to be filtered along the filter inlet surface 11 and a collection channel 17 for collecting the filtered gases exiting at the filter outlet surface 13. The course of the flow of the gases is schematically illustrated in part in the figures by means of a flow arrow 19. In accordance with FIGS. 1a to 4e, the gases are conveyed into the housing 3 via an air conveyor 21 in the form of a fan 21 arranged at the inlet opening 5 and conveyed through the filtering apparatus 9.

The activated-charcoal mats 9 are fastened to a support mesh 23 (e.g. a wire mesh); the support mesh 23 is arranged behind the filtering apparatus 9 in the direction of flow in accordance with FIGS. 1a to 4e. Because the support mesh 23 of the filtering apparatus 9 is downstream with reference to the direction of flow, the filtering apparatus 9 is pressed against the support mesh 23 via the flow pressure of the gases and is consequently reliably held in place by same. The activated-charcoal mat 9 is fastened to the support mesh 23 so that the activated-charcoal mat 9 will also securely remain in position on the support mesh 23 when the gas filter device 1 is at rest (i.e. with a shut-off fan 21). Instead of the downstream support mesh 23, or in addition to it, a support mesh (see e.g. FIG. 5) that is upstream of the activated-charcoal mat 9 with reference to the direction of flow can also be provided that is arranged in front of the activated-charcoal mat 9 in the direction of flow (e.g. to the effect that the activated-charcoal mat 9 is clamped between the upstream and the downstream support mesh).

The gas filter device 1 has, moreover, a heating device 25 to heat up the gases to be filtered. The heating device 25 is arranged in front of the filtering apparatus 9 with reference to the direction of flow in the flow path of the gases to be filtered in the distribution channel 15, for instance on the filter inlet surface 11 in direct contact with the filtering apparatus 9. The heating device 25 is designed in such a way that heating power that is uniform over the entire area is provided by it; the heating device 25 spans the entire filter inlet surface 11, as an example, and this consequently makes it possible to bring the gases entering the filtering apparatus 9 up to a temperature that is spatially uniform across the entire filter inlet surface 11.

The heating device 25 is designed to be an electrical heating device, for instance in the form of a metallic heating network with heating wires here. There can also be provisions, however, for the heating device 25 to be realized in the form of a capillary-tube-mat heating element. Alternatively, or in addition, one or more (e.g. electrical) heating elements (similar to those in clothes dryers) can be arranged at the inlet opening 5 or at the output cross section of the fan 21, e.g. inserted in same; good equalization of the air temperature is required here, however—at least when a heating element of this type is used alone. Uniform heating of the entire gas flow to be filtered is possible via the heating device 25 in such a way that adherence is kept with the living conditions and metabolizing conditions (temperature and relative humidity) required for the microbes or microorganisms.

One activated-charcoal mat as a section of the filtering apparatus 9, a support mesh 23 and a heating element of the heating device 25 form a packet in each case; this packet can be swiveled around a horizontal axis (not shown) arranged on the lower end section of the packet in the designs according to FIGS. 2 to 4e after the housing 3 is opened, and the filtering apparatus 9 can be replaced in an uncomplicated way during maintenance work by swiveling the packet out of a vertical orientation into a horizontal orientation or, as the case may be, folding it outward, and then replacing the filtering apparatus 9.

In accordance with FIGS. 1a to 4e, the housing 3 has thermal insulation or a thermal insulation layer 27 on its outer wall. The thermal insulation 27 prevents condensate from freezing on the outer wall of the housing 3 and consequently the formation of ice in the interior of the gas filter device 1. The gas filter device 1 is designed in such a way (via the corresponding design of the air conveyor 21 and the thermal insulation 27) that the activated-charcoal mats 9 are thermally decoupled from the external environment to a very great extent. The filtering apparatus 9 is also shielded against outside temperatures (that are usually too low) by flow-related shielding, in addition to shielding via the thermal insulation 27, by designing the outlet opening 7 to have an outlet cross section that brings about a situation in which the excess pressure of the gases at the outlet opening 7 is greater than the wind pressure at the height of the outlet opening 7.

The housing 3 is designed in such a way that condensate arising on the interior of the outer wall of the housing 3 can flow out of the housing 3 via a condensate runoff, e.g. flow out in a downwards direction, and can be discharged from the housing 3 through drain openings provided for that. The thermal insulation 27 can limit or prevent the use of solar heat (e.g. in summer) acting on the housing 3 to heat up the gases, though, so the gas filter device 1 can also be designed without thermal insulation—in that case, the gas filter device 1 can have one or more vortex generators (not shown), via which hotter and colder gas portions can be mixed with one another, thereby improving the heat transfer, so that an even temperature can be ensured in the gases.

The gas filter device 1 has an inflow channel 29 running from the inlet opening 5 to the filter inlet surface 11 to feed the gases to be filtered to the activated-charcoal mat 9, and an outflow channel 31 running from the filter outlet surface 13 to the outlet opening 7 to draw off the filtered gases from the activated-charcoal mat 9. The distribution channel 15 is the section of the inflow channel 29 along which the gases to be filtered are distributed over the filter inlet surface 11 (and along which the filter inlet surface 11 forms a boundary surface of the inflow channel 29). The collection channel 17 is the section of the outflow channel 31 along which the filtered gases exiting the filter outlet surface 13 are collected (and along which the filter outlet surface 13 forms a boundary surface of the outflow channel 31). As an example, in the gas filter device 1 in accordance with FIG. 1a, the distribution channel 15 is identical to the inflow channel 29 and the collection channel 17 is a partial section of the outflow channel 31; in the gas filter device 1 in accordance with FIG. 2, the distribution channel 15 is a partial section of the inflow channel 29 and the collection channel 17 is a partial section of the outflow channel 31.

The gas filter device 1 in accordance with the designs according to FIGS. 1a to 4e can be designed with a rectangular or round cross section, for instance, in the horizontal plane perpendicular to the z axis or height direction and can be rotationally symmetric, for example, with regard to its height direction. When the gas filter device 1 has a round design, the activated-charcoal mat or the activated-charcoal mats 9 can be laid with offset abutting ends with their long side in the direction of the circumference.

In accordance with FIGS. 1a to 4e, the distribution channel 15 is designed in such a way that the gases to be cleaned flow along at least a portion of the filter inlet surface 11 in each case before entering the filtering apparatus 9; moreover, the collection channel 17 is designed in such a way that the gases to be cleaned flow along at least a portion of the filter outlet surface 13 after exiting the filtering apparatus 9. A major portion of the overall volume of the gas filter device 1 can be filed out by the filter elements or activated-charcoal mats 9 with this arrangement, and the largest possible active filter area—with reference to the overall volume of the gas filter device—can consequently be provided. The gas filter device 1 is designed in such a way that the output velocity at which the filtered gases leave the outlet opening 7 is sufficiently large (but not too large, because excess noise development could otherwise come about).

The different designs of the distribution channel and the collection channel of the gas filter devices in accordance with FIGS. 1a to 4e will be explained below.

The gas filter devices 1 in accordance with FIGS. 1a and 1b are designed in such a way that the flow is guided from the inside to the outside through the filtering apparatus or activated-charcoal mat 9; the distribution channel 15 is formed between two activated-charcoal mat sections 9 (or between two sections of the filter inlet surface 11), and the collection channel 17 is formed between the filter outlet surface 13 and a section of the outer wall or circumferential wall of the housing 3. In accordance with FIGS. 1a and 1b, both the distribution channel 15 and the collection channel 17 are designed with a constant cross section running along the direction of flow of the gases (that is to say running along their longitudinal direction in parallel with the z direction). The gas filter device in accordance with FIGS. 1a and 1b differ to the effect that the outlet opening 7 is arranged in the upper end section or roof area with regard to the gas filter device 1 according to FIG. 1a, whereas the outlet opening 7 is arranged in the lower end section or floor area in accordance with FIG. 1b, and the flow is consequently guided in different ways in these two gas filter devices, and the filtered gases are therefore also mixed differently with the environmental are (with a dilution of the residues). In accordance with the gas filter device 1 according to FIG. 1a, a higher flow velocity can be made possible, but the smell coming out of the outlet opening 7 is more likely at the height of a human nose.

In each of the embodiments in accordance with FIGS. 2 to 4e, the gas filter device 1 is designed with a spatially varying cross section via the design of the distribution channel 15 and/or the collection channel 17 in such a way that a very even distribution of the flow velocity (i.e. the flow velocity at which the gases flow through the filtering apparatus) across the entire surface of the activated-charcoal mat 9 or over the entire filter inlet surface 11.

Figure 2:
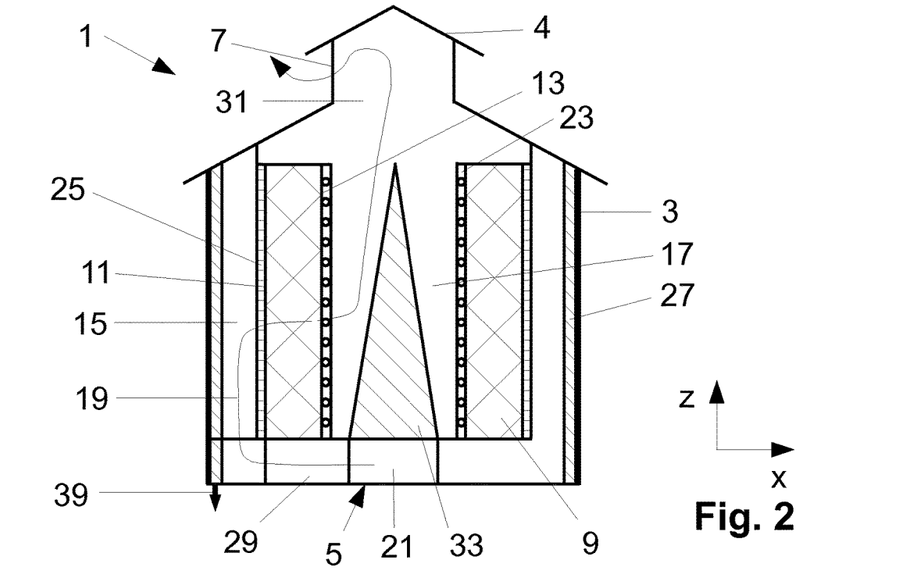
FIG. 2 shows a sectional view of a gas filter device according to one embodiment.
Figure 3:
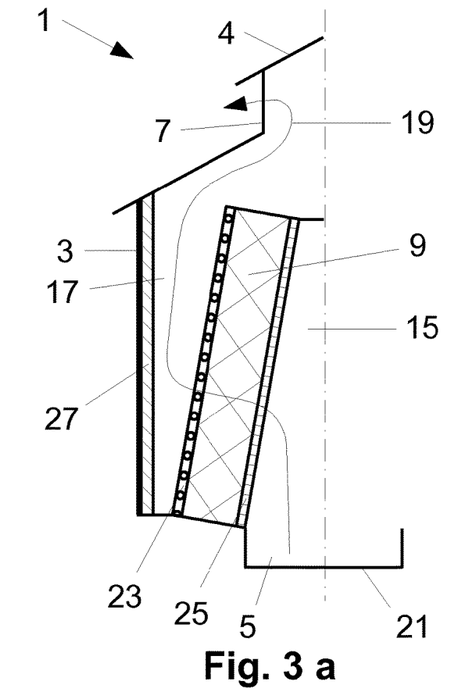
FIG. 3a shows a sectional view of a gas filter device according to a further embodiment.
FIG. 3b shows a sectional view of a gas filter device according to a further embodiment.

In the embodiment in accordance with FIG. 2, the distribution channel 15 is designed to have a constant cross section; in contrast, the cross section of the collection channel 17 varies along the direction of flow of the gases flowing through it to the effect that the collection channel has an opening angle of 3° along this direction. In particular, the collection channel 17 is designed with a cross section that evenly increases along its entire length (in the direction of flow of the gases flowing through it); the cross section of the collection channel 17 is varied via a molded part 33 arranged in the flow path of the gases. The molded part 33 has a triangular cross section in a vertical section (i.e. in accordance with the coordinate system parallel to the xz plane illustrated in FIG. 2) and can be designed to be a pyramid, prism, cone or truncated cone, for example. The molded part 33 can, as an example, be designed to be a pyramid with a triangular, square, rectangular or general polygonal base area; the design as a pyramid with a polygonal base area is especially advantageous in cases in which the filter elements or the activated-charcoal mats 9—e.g. for weight reasons—are divided up. In the gas filter device 1 in accordance with FIG. 2, the flow is guided through the activated-charcoal mat 9 from the outside to the inside; the distribution channel 15 is formed between the filter inlet surface 11 and a section of the wall of the housing 3, and the collection channel 17 is formed between the filter outlet surface 13 and a side surface of the molded part 33. Because the collection channel 17 is designed with an increasing cross section, an equalization of the flow velocity is achieved across the surface of the activated-charcoal mat 9. In the gas filter device 1 in accordance with FIG. 2, the fan 21 has a vertical axis and is designed without a spiral housing (in which condensate could accumulate). In accordance with this embodiment, the fan 21 has a radial rotor disk and a diffuser with blades or without blades connected downstream from same; the diffusor with blades acts as a guide wheel. The flow entering the fan 21 is delayed and equalized in the diffusor without blades directly downstream from the rotor disk, the diffusor with blades acting as a guide wheel and the diffusor connected to the guide wheel. Moreover, a condensate runoff 39 is illustrated in FIG. 2.

In the embodiment in accordance with FIG. 3a, the distribution channel 15 is designed with a cross section that decreases in the direction of flow of the gases flowing through it and the collection channel 17 has an cross section increasing along the direction of flow of the gases flowing through it; The cross-section variation of these two channels is realized by arranging the filtering apparatus in the form of the activated-charcoal mat 9 at an angle (i.e. not in parallel) to the circumference wall of the housing 3. FIG. 3b illustrates a gas filter device 1 with a flow guided from the inside to the outside; the collection channel 17 is designed with a cross section that increases on a step-by-step basis via a molded part 35 that is rectangular in the vertical section that is shown.

Figure 4:
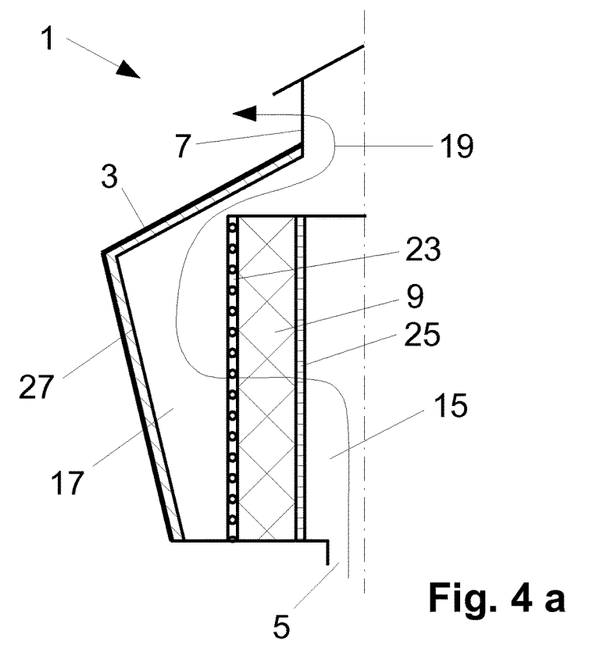
FIG. 4a shows a sectional view of a gas filter device according to a further embodiment.
FIG. 4b shows a sectional view of a gas filter device according to a further embodiment.
FIG. 4c shows a sectional view of a gas filter device according to a further embodiment.
FIG. 4d shows a sectional view of a gas filter device according to a further embodiment.
FIG. 4e shows a sectional view of a gas filter device according to a further embodiment.

FIGS. 4a to 4e illustrate further possibilities for designing a collection channel 17 with a cross section that increases along the direction of flow via a design of the housing 3 (FIGS. 4a, 4d, 4e) or the thermal insulation 27 (FIG. 4c)

with a corresponding form and/or via a molded part 33 with a corresponding form (FIG. 4b) arranged in the flow path of the gases. Moreover, in accordance with FIG. 4e, the distribution channel 15 is designed with a decreasing cross section via a molded part 33. In FIG. 4b, a heating element 37 arranged at the entrance of the distribution channel 15 is provided in addition to the heating device 25 arranged in contact with the filter inlet surface 11. In the design forms according to FIGS. 2 to 4e, the (maximum) cross section of the collection channel and the (maximum) cross section of the distribution channel are smaller than 5% of the area of the activated-charcoal mat 9 or, as the case may be, the filter inlet surface 11.

The heating device 25 can, as shown in FIG. 4b, be arranged in the housing 3 but also beneath the housing 3.

FIGS. 5 to 8 illustrate embodiments in which the gas filter device 1 is integrated into a building 45; in particular, no separate housing is required for the gas filter device 1 and the functions of thermal insulation, temperature control and air conveyance are realized at least in part by the building 45. The building 45 has, among other things, a roof 41 with a thermal insulation layer and a building wall 42; the roof 41 and the building wall 42 form a building room 44. A filtering apparatus 9, a heating device 25 and a support mesh 23 are connected with one another in each case, forming a filter packet 40. In accordance with the design forms according to FIGS. 5 to 8, the collection channel 17 is designed in each case with a cross section that increases in the direction of flow of the gases flowing through it.

Figure 5:
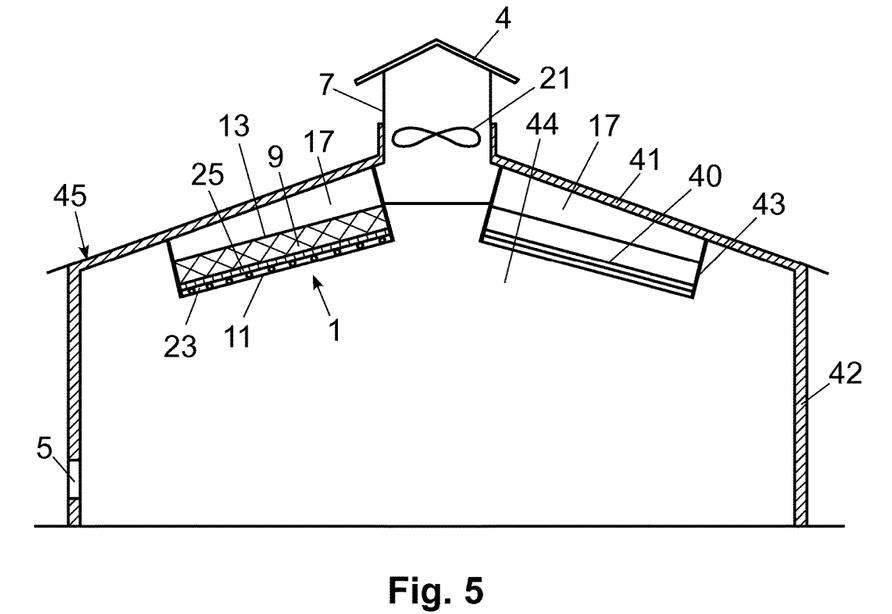
FIG. 5 shows a sectional view of a gas filter device integrated into the interior of a building according to one embodiment.

In accordance with FIG. 5, the filter packets 40 are attached via a holding fixture 43 to the roof 41 of the building 45 in such a way that the collection channel 17 is formed between the inside of the roof 41 and the filter outlet surface 13. In accordance with FIG. 6, the filter packets 40 are attached via a holding fixture 43 to the wall 42 in such a way that the collection channel 17 is formed between the inside of the wall 42 and the filter outlet surface 13. In accordance with FIG. 7, the filter packet 40 is attached to the wall 42 in such a way that the distribution channel 15 is formed between the outside of the wall 42 and the filter inlet surface 11. In accordance with FIG. 8, the filter packets 40 are arranged under the ventilation hood 4 of the building 45 in such a way that the collection channel 17 is formed between the ventilation hood 4 and the filter outlet surface 13.

Figure 6:
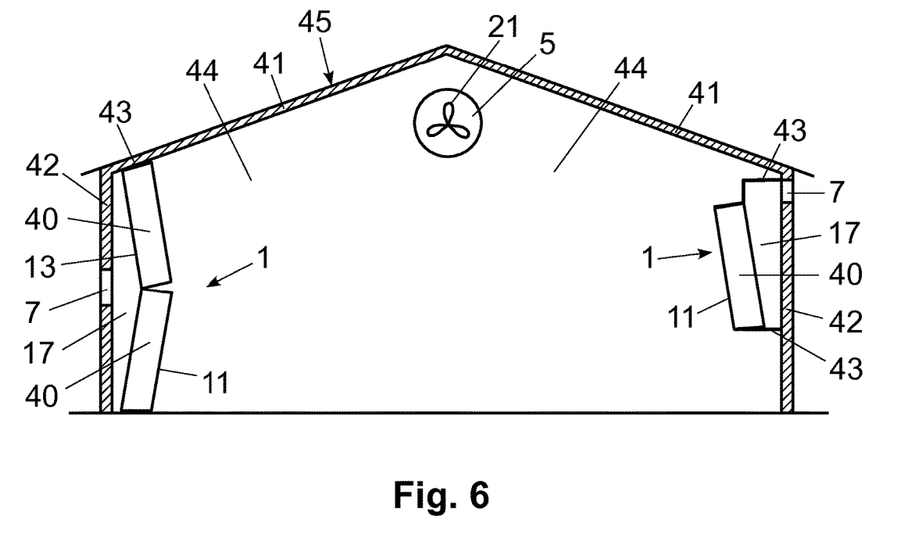
FIG. 6 shows a sectional view of a gas filter device integrated into the interior of a building according to a further embodiment.
Figure 8:
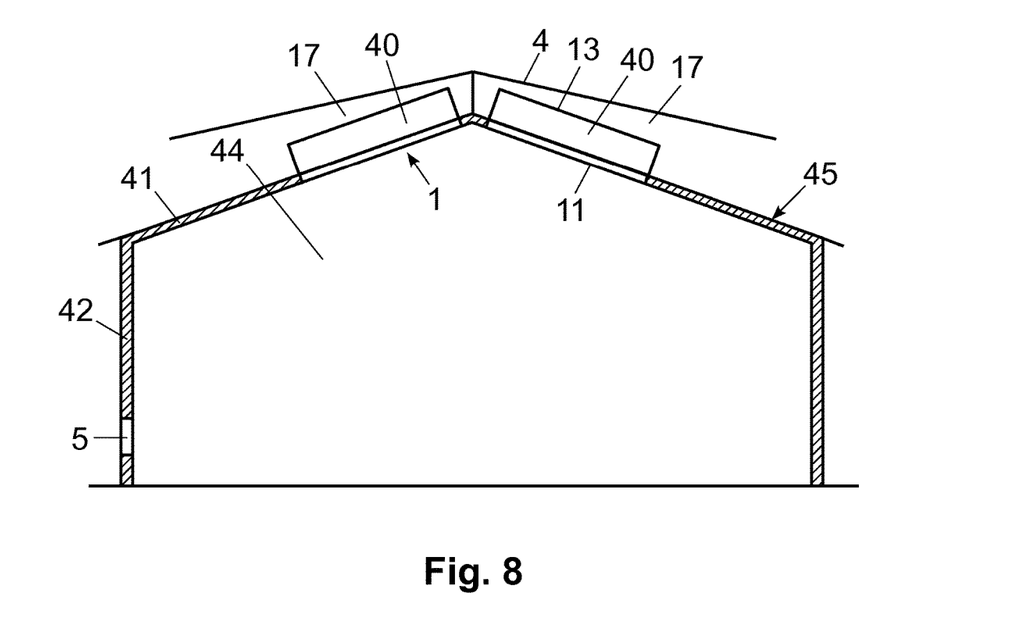
FIG. 8 shows a sectional view of a gas filter device integrated on a building according to a further embodiment.

In accordance with FIGS. 5, 6 and 8, the distribution channel 15 is formed by the room 44 of the building 45. A very uniform velocity distribution over the filter area can be achieved because of that when the cross section of the collection channel increases in a suitable way in the direction of flow. The arrangement of the filter packets 40 in the interior of the building 45 (especially in accordance with FIG. 6) is therefore significantly more advantageous. In addition, the filter packets 40 are protected against wanton damage in that way.

Figure 7:
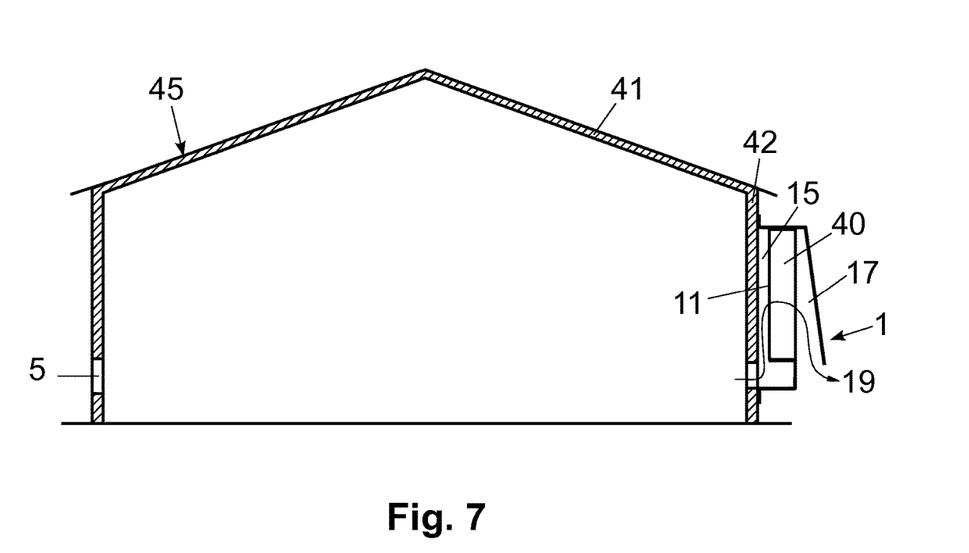
FIG. 7 shows a sectional view of a gas filter device integrated outside of a building according to one embodiment.

If the filter packet 40 is put on the building 45 externally (such as in FIG. 7, for instance), higher expenses result to achieve an even velocity distribution over the width. If a great deal of heat develops in the building, the natural flow of air may suffice and a fan will not have to be installed (FIGS. 7, 8). The filter packets are directly integrated into the roof 41 in FIG. 8.

One, two or several filter packets can be arranged depending on the task at hand with regard to the gas volumetric flow rate, the service life of the filter packets or filter cells etc.

LIST OF REFERENCE NUMERALS

1 Gas filter device
3 Housing
4 Ventilation hood/roof section of the housing
5 Inlet opening
7 Outlet opening
9 Filtering apparatus/activated-charcoal mat supplied with microorganisms
11 Filter inlet surface
13 Filter outlet surface
15 Distribution channel
17 Collection channel
19 Course of the flow
21 Air conveyor/fan
23 Support mesh
25 Heating device
27 Thermal insulation layer
29 Inflow channel
31 Outflow channel
33 Molded part with a triangular cross section
35 Molded part with a rectangular cross section
37 Heating element
39 Condensate runoff
40 Filter packet
41 Roof with thermal insulation layer
42 Building wall
43 Holding fixture
44 Distribution area/building room
45 Building

The invention claimed is:

1. A gas filter device (1) for filtering contaminants out of gases, wherein the gas filter device is a rain-tight freestanding cell, comprising:
   a filtering apparatus (9) for filtering the gases, wherein the gases enter the filtering apparatus at a filter inlet surface (11), flow through the filtering apparatus, and exit the filtering apparatus at a filter outlet surface (13), and
   a distribution channel (15) for distributing the gases to be filtered along the filter inlet surface (11), wherein the filter inlet surface forms a permeable, lateral boundary surface of the distribution channel, and a collection channel (17) for collecting the filtered gases exiting at the filter outlet surface (13), wherein the filter outlet surface forms a permeable, lateral boundary surface of the collection channel,
   wherein the cross section of the collection channel (17) increases in the direction of flow of the gases, and the distribution channel (15) exhibits a constant cross section, and
   a heating device (25, 37) for heating the gases to be filtered in order to lower the relative moisture content of said gases before entering the filtering apparatus, wherein the heating device is located within the flow path of the gases in front of the filtering apparatus (9) with respect to the direction of flow and is extending across the entire cross section of the flow.

2. The gas filter device according to claim 1, wherein the filtering apparatus (9) is supplied with microorganisms to break down the contaminants.

3. The gas filter device according to claim 2, wherein the filtering apparatus (9) has an activated-charcoal layer (9) that is supplied with microorganisms.

4. The gas filter device according to claim 1, wherein the heating device (25, 37) is an electrically operated heating device.

5. The gas filter device according to claim 1, wherein the distribution channel (15) distributes the gases along the filter inlet surface (11) before said gases enter the filtering apparatus (9) and/or the collection channel (17) collects the gases along the filter outlet surface (13) after said gases exit the filtering apparatus (9).

6. The gas filter device according to claim 1, wherein the cross section of the collection channel (17) is varied via a molded part (33, 35) arranged in the flow path of the gases.

7. The gas filter device according to claim 1, wherein the mean value of the cross-sectional area of the distribution channel (15) and/or of the collection channel (17) is smaller than 5% of the filter inlet surface (11).

8. The gas filter device according to claim 1, having an air conveyor (21) for conveying the gases through the filtering apparatus (9).

9. The gas filter device according to claim 1, wherein the filtering apparatus (9), the distribution channel (15), the collection channel (17) and the heating device (25, 37) are arranged in a housing (3), and wherein at least a portion of the external wall of the housing (3) has thermal insulation (27).

10. The gas filter device according to claim 1, wherein the collection channel (17) is has an opening angle between 2° and 10°.

11. The gas filter device according to claim 1, wherein the gas filter device has a support mesh, at least one section of the filtering apparatus is fastened in a detachable way to the support mesh, forming a packet, and the packet can be swiveled around a horizontal axis.

* * * * *